(12) United States Patent
Chafe et al.

(10) Patent No.: US 11,045,150 B2
(45) Date of Patent: *Jun. 29, 2021

(54) METHOD OF SONIFYING BRAIN ELECTRICAL ACTIVITY

(71) Applicant: The Board of Trustees of the Leland Stanford Junior University, Stanford, CA (US)

(72) Inventors: Christopher D. Chafe, Woodside, CA (US); Josef Parvizi, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 423 days.

This patent is subject to a terminal disclaimer.

(21) Appl. No.: 16/154,058

(22) Filed: Oct. 8, 2018

(65) Prior Publication Data

US 2019/0038237 A1 Feb. 7, 2019

Related U.S. Application Data

(63) Continuation of application No. 13/905,377, filed on May 30, 2013, now Pat. No. 10,136,862.

(60) Provisional application No. 61/653,370, filed on May 30, 2012.

(51) Int. Cl.
*A61B 5/369* (2021.01)
*A61B 5/00* (2006.01)
*A61B 5/316* (2021.01)

(52) U.S. Cl.
CPC ............ *A61B 5/7415* (2013.01); *A61B 5/316* (2021.01); *A61B 5/369* (2021.01); *A61B 5/4094* (2013.01)

(58) Field of Classification Search
CPC .............. A61B 5/741–7415; A61B 5/369–386
See application file for complete search history.

(56) References Cited

U.S. PATENT DOCUMENTS 10,136,862 B2 * 11/2018 Chafe .................... A61B 5/369

* cited by examiner

*Primary Examiner* — Meredith Weare
(74) *Attorney, Agent, or Firm* — Lumen Patent Firm (57) ABSTRACT

A digital processor system having one or more processors and memory obtains a time-domain signal representing brain activity, the time-domain signal having a time varying signal value. The system concurrently generates a set of acoustic parameters, including a plurality of time-varying acoustic parameters, where one or more of the plurality of time-varying acoustic parameters is modulated in accordance with at least the signal value of the time-domain signal. The system combines the concurrently generated set of acoustic parameters to produce a representation of an acoustic signal corresponding to the time-domain signal, where the acoustic signal, in audible form, manifests one or more audibly discernible variations across a plurality of stages of a brain activity event.

21 Claims, 8 Drawing Sheets

502: Perform method 400 (see Figures 4A-4C) concurrently on a plurality of time-domain signals representing brain activity at a plurality of distinct locations in a brain to produce representations of a plurality of acoustic signals, each corresponding to one of the plurality of distinct locations in the brain

504: The plurality of acoustic signals, each corresponding to one of the plurality of distinct locations in the brain, comprise audibly distinct acoustic signals

506: The plurality of acoustic signals, each corresponding to one of the plurality of distinct locations in the brain, comprise audibly distinct sonic identities

Figure 5

METHOD OF SONIFYING BRAIN ELECTRICAL ACTIVITY

CROSS-REFERENCE TO RELATED APPLICATIONS

This application is a continuation of U.S. patent application Ser. No. 13/905,377 filed May 30, 2013, which is incorporated herein by reference. U.S. patent application Ser. No. 13/905,377 filed May 30, 2013 claims priority from U.S. Provisional Application 61/653,370 filed May 30, 2012, which is incorporated herein by reference.

FIELD OF THE INVENTION

The disclosed embodiments relate generally to the field of detecting brain activity, and in particular, to a system and method of sonifying brain electrical activity.

BACKGROUND OF THE INVENTION

The ability to measure location-specific brain signals is beneficial for medical and diagnostic applications as well as for scientific research. From a diagnostic point of view, measuring brain signals helps to ascertain brain activity related to abnormal brain function, to monitor spatial and/or temporal progression of brain disease, and to aid surgical or nonsurgical intervention by localizing disease-sites in the brain. From a scientific perspective, the ability to measure and study brain signals facilitates scientific research aimed at understanding the structure and function of the human brain.

SUMMARY OF THE INVENTION

Traditional approaches to measuring location-specific brain signals involve recording and visually displaying electrical signals acquired from the brain. When represented in visual or graphical form, subtle features and attributes—and subtle changes in features and attributes—of the brain signals may not be easily discernible. However, when sonified or converted to auditory form, these subtle features and attributes can become more apparent. Furthermore, sonification methodologies that transform the electrical signals acquired from the human brain into vocal patterns and vocal parameters—and changes in vocal patterns and vocal parameters—that resemble human voice, make it easier to discern subtleties in the underlying electrical signals corresponding to brain activity, upon auditory inspection.

Additionally, an aural representation (resembling human vocal patterns) or auditory play-back of the electrical signals acquired from the human brain enables "super-scanning" or rapid analysis of long-term recordings (e.g., recordings acquired over several days) by auditory inspection, when compared to visual inspection or scanning-by-eye of the raw electrical recordings.

Accordingly, some embodiments provide a system and method for sonifying brain signals, including concurrently generating a set of acoustic parameters—including one or more time-varying acoustic parameters (such as a frequency-control parameter, a vowel-control parameter, an intensity-control parameter)—corresponding to the brain signal, and combining the concurrently generated set of acoustic parameters to produce a representation of an acoustic signal.

In some embodiments, a method is performed at a computer system having one or more processors and memory storing one or more programs for execution by the one or more processors so as to perform the method. The method includes obtaining a time-domain signal representing brain activity, the time-domain signal having a time varying signal value. The method further includes concurrently generating a set of acoustic parameters, including a plurality of time-varying acoustic parameters. One or more of the plurality of time-varying acoustic parameters is modulated in accordance with at least the signal value of the time-domain signal. The method also includes combining the concurrently generated set of acoustic parameters to produce a representation of an acoustic signal corresponding to the time-domain signal, where the acoustic signal, in audible form, manifests one or more audibly discernible variations across a plurality of stages of a brain activity event.

In accordance with some embodiments, a computer system (e.g., a client system or server system) includes one or more processors, memory, and one or more programs; the one or more programs are stored in memory and configured to be executed by the one or more processors and the one or more programs include instructions for performing the operations of the method described above. In accordance with some embodiments, a non-transitory computer readable storage medium has stored therein instructions which when executed by one or more processors, cause a computer system (e.g., a client system or server system) to perform the operations of the methods described above.

BRIEF DESCRIPTION OF THE DRAWINGS

Like reference numerals refer to corresponding parts throughout the drawings.

DETAILED DESCRIPTION

It will be understood that, although the terms "first," "second," etc. are optionally used herein to describe various elements, these elements should not be limited by these terms. These terms are only used to distinguish one element from another. For example, a first sensor could be termed a second sensor, and, similarly, a second sensor could be termed a first sensor, without changing the meaning of the description, so long as all occurrences of the "first sensor" are renamed consistently and all occurrences of the second sensor are renamed consistently. The first sensor and the second sensor are both sensors, but they are not the same sensor.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

Reference will now be made in detail to various embodiments, examples of which are illustrated in the accompanying drawings. In the following detailed description, numerous specific details are set forth in order to provide a thorough understanding of the invention and the described embodiments. However, the invention is optionally practiced without these specific details. In other instances, well-known methods, procedures, components, and circuits have not been described in detail so as not to unnecessarily obscure aspects of the embodiments.

Figure 1:
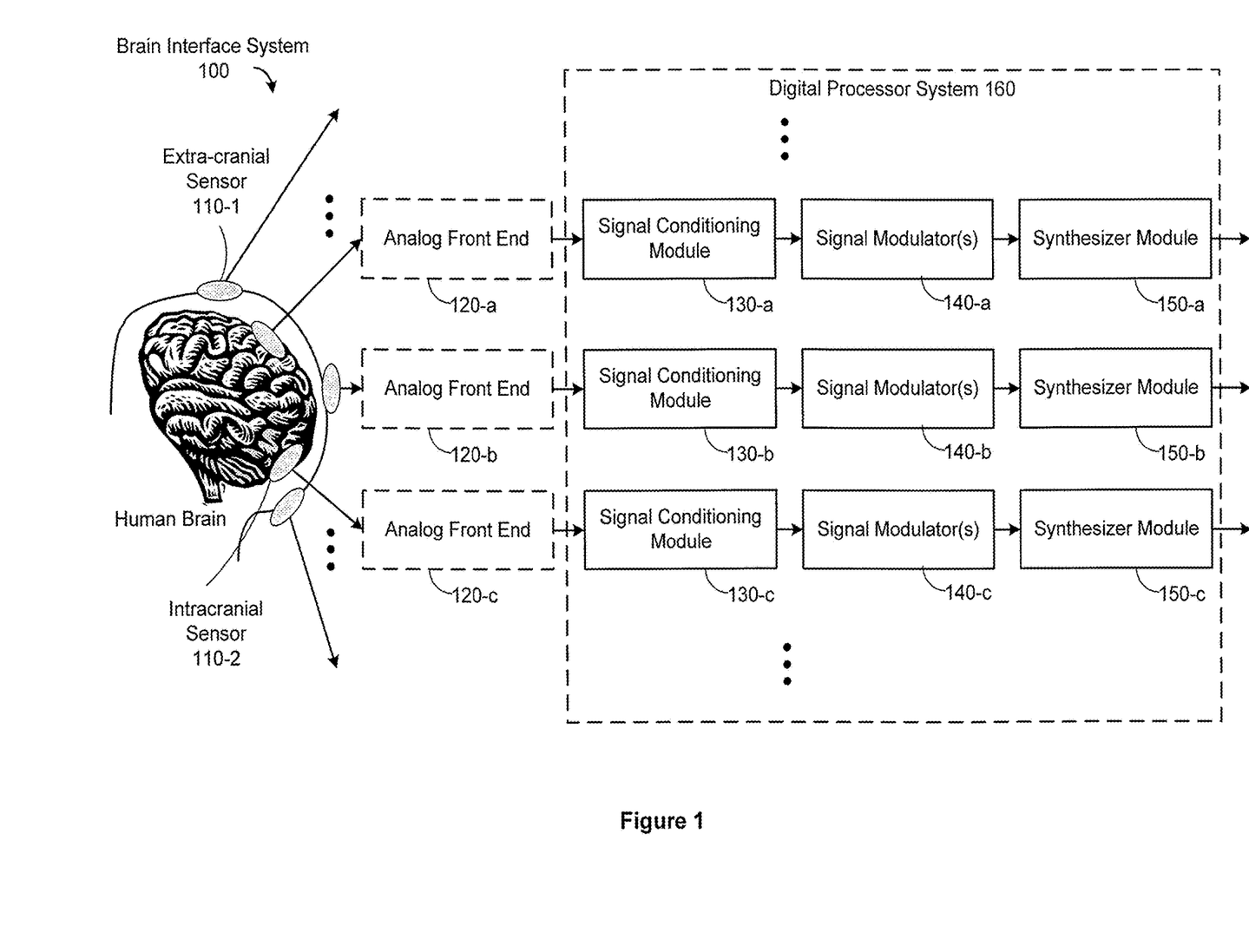
FIG. 1 illustrates a brain interface system for acquiring and processing signals from a human brain, in accordance with some embodiments.

FIG. 1 illustrates Brain Interface System 100 for sensing, acquiring and processing signals obtained from a human brain to produce a representation of an acoustic signal corresponding to one or more brain signals (e.g., representing brain activity). In some embodiments, Brain Interface System 100 is deployed in clinical settings (e.g., during or before surgical interventions; during diagnosis and/or treatment of conditions, such as epileptic seizures) for aural (e.g., auditory) measurement or monitoring of brain activity. In some embodiments, as shown in FIG. 1, Brain Interface System 100 includes one or more Sensor(s) 110, optionally includes one or more Analog Front End(s) 120 (e.g., one or more analog front end modules), and Digital Processor System 160 (herein often called Digital Processor 160 for ease of reference).

In some embodiments, Sensor(s) 110 are provided to interface with a human brain to obtain (e.g., sense and/or acquire) sensor time-domain signals (e.g., Sensor Time-Domain Signal 201, FIG. 2A) corresponding to brain electrical activity. For example, signals (e.g., Sensor Time-Domain Signal 201, FIG. 2A) corresponding to brain electrical activity are obtained from the human brain and correspond to electrical signals obtained from a single neuron or from a plurality of neurons. In some embodiments, Sensor(s) 110 include(s) one or more sensors affixed (e.g., taped, attached, glued) externally to a human scalp (e.g., Extra-cranial Sensor 110-1). For example, Extra-cranial Sensor 110-1 include(s) an electrode (e.g., Electroencephalography, EEG electrode) or a plurality of electrodes (e.g., Electroencephalography, EEG electrodes) affixed externally to the scalp (e.g., glued to the skin via conductive gel), or more generally positioned at respective positions external to the scalp. Alternatively, dry electrodes can be used in some implementations. The signals obtained from an extra-cranial sensor 110-1 are sometimes herein called EEG signals or time-domain EEG signals.

In some embodiments, Sensor(s) 110 include(s) a sensor embedded in a particular location of a brain (e.g., Intra-cranial Sensor 110-2). For example, Intra-cranial Sensor 110-2 is formed (e.g., fabricated) on a needle embedded in a particular location of the brain with one or more sensing elements located along the length and/or circumference of the needle. In some embodiments, a plurality of Sensor(s) 110 (e.g., Intra-cranial Sensor 110-2) are formed (e.g., fabricated) on a single needle (e.g., 8 instances of Sensor(s) 110 or 8 sensing elements are formed on a single needle) embedded in a particular location of a brain. In some embodiments, Intracranial Sensor 110-2 includes intracranial depth electrodes implanted in the brain at a plurality of locations to monitor electrical activity in the brain at the plurality of locations. In some embodiments, a plurality of Sensor(s) 110 (e.g., 8-80 sensors) is embedded across a plurality of regions of interest in the brain. In such embodiments, individual sensors are sensitive to small electrical potential changes caused by neural signaling at corresponding locations in the brain (or in corresponding regions of the brain). In some implementations, the observed signal (e.g., Sensor Time-Domain Signal 201, FIG. 2A) obtained from each Sensor 110 (e.g., Intracranial Sensor 110-2) represents the aggregate activity (e.g., corresponding to 10,000 neurons) in the region in proximity to the respective sensor (e.g., Intra-cranial Sensor 110-2).

In some embodiments, Sensor(s) 110 sense voltages corresponding to brain electrical activity. In alternative embodiments, Sensor(s) 110 sense electrical currents corresponding to brain electrical activity. In some implementations, Sensor(s) 110 sense differential voltages (e.g., differences in voltage values) between two measurement locations (e.g., between two sensing elements). For example, when Sensor(s) 110 (e.g., Intracranial Sensor 110-2) are formed (e.g., fabricated) on a needle embedded in a particular location of the brain, Sensor(s) 110 sense differential voltages between two sensing elements located along the length and/or circumference of the needle. In some implementations, a "bipolar montage" is constructed by referencing each of a set of sensing elements to its nearest neighbor (e.g., an adjoining sensing element) to produce a corresponding set of differential voltage signals, each of which is a respective Sensor Time-Domain Signal 201, FIG. 2A. In such embodiments, a respective Sensor 110 comprises a pair of neighboring sensor elements, and a set of N Sensors 110 (where N is an integer greater than or equal to two) is formed from N or N+1 sensor elements (depending on the configuration of the sensor elements). For example, a needle with 8 (or other integer number, M) sensor elements would form seven or eight (or M−1 or M) Sensors 110, depending on the physical layout or configuration of the 8 sensor elements. In some embodiments, synchronous brain activity with small phase differences in (e.g., between) measured voltages is measured across sensing elements.

Figure 2A:
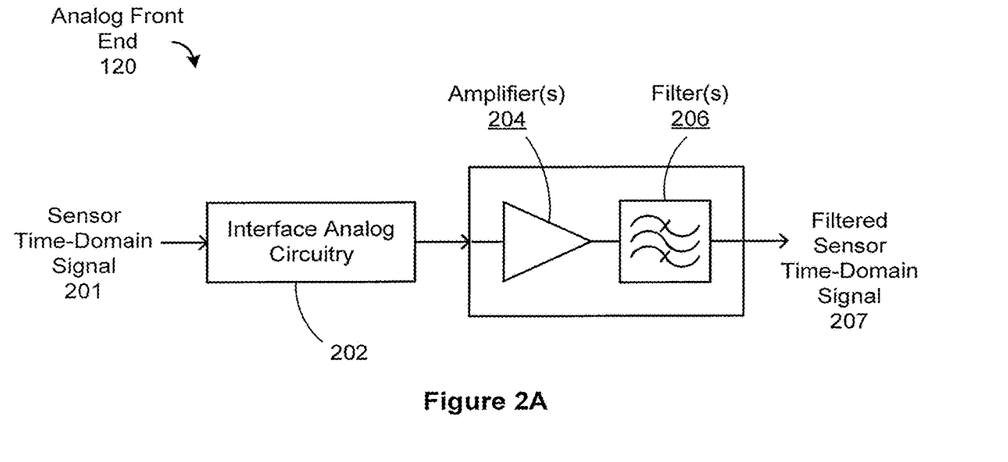
FIG. 2A is a block diagram illustrating an analog front end used for pre-processing electrical signals obtained from a human brain, in accordance with some embodiments.

In some embodiments, arrays of sensors (e.g., Sensor(s) 110) are designed to produce a plurality of sensor time-domain signals (e.g., Sensor Time-Domain Signal 201, FIG. 2A). In some embodiments, sensor time-domain signals (e.g., Sensor Time-Domain Signal 201, FIG. 2A) include wideband features including high-gamma bursts in the range of 80-150 Hz. In some embodiments, Sensor(s) 110 embedded in a particular location of the brain are additionally configured to dispense medication to localized portions of the brain. In some embodiments, sensor time-domain signals (e.g., Sensor Time-Domain Signal 201, FIG. 2A) include frequencies (sometimes called frequency components) below (e.g., lower than or in the lowest ranges of) the human audible frequency-range.

In some implementations, Analog Front End 120 receives sensor time-domain signals (e.g., Sensor Time-Domain Signal 201, FIG. 2A) from Sensor(s) 110 and optionally pre-processes the sensor time-domain signals to produce filtered sensor time-domain signals (e.g., Filtered Sensor Time-Domain Signals 207, FIG. 2A). In some embodiments, a separate (e.g., independent) analog front end is provided for interfacing with each of a set of Sensor(s) 110. In such embodiments, Brain Interface System 100 comprises a plurality of analog front end modules (e.g., Analog Front End 120-a, Analog Front End 120-b, Analog Front End 120-c, . . . ) for interfacing with a plurality of Sensor(s) 110.

As shown in FIG. 1, Brain Interface System 100 includes Digital Processor 160 for processing signals obtained from the human brain (e.g., signals corresponding to electrical activity of the brain), optionally after the signals are pre-processed by Analog Front End 120. Digital Processor 160 includes Signal Conditioning Module 130, Signal Modulator(s) 140, and Synthesizer Module 150. In some embodiments, a separate (e.g., independent) signal conditioning module, a separate (e.g., independent) signal modulator, and/or a separate (e.g., independent) synthesizer module is provided for interfacing with each Sensor 110 in a set of two or more Sensors 110 (optionally through a separate analog front end module). In such embodiments, Brain Interface System 100 comprises a plurality of signal conditioning modules (e.g., Signal Conditioning Module 130-a, Signal Conditioning Module 130-b, Signal Conditioning Module 130-c, . . . ), a plurality of signal modulator(s) (e.g., Signal Modulator(s) 140-a, Signal Modulator(s) 140-b, Signal Modulator(s) 140-c, . . . ), and/or a plurality of synthesizer modules (e.g., Synthesizer Module 150-a, Synthesizer Module 150-b, Synthesizer Module 150-c, . . . ) for interfacing with a plurality of Sensors 110 and processing signals obtained from those sensors.

In some embodiments, a respective Signal Conditioning Module 130 includes a data convertor (e.g., an analog to digital convertor for converting an analog filtered sensor time-domain signal obtained from Sensor(s) 110 to a corresponding digital representation), an upsampler and a digital low-pass filter. In some implementations, Signal Modulators 140 receive the digitized time-domain signals output by Signal Conditioning Modules 130, and concurrently generate a set of acoustic parameters, including a plurality of time-varying acoustic parameters from (e.g., using) the digitized time-domain signals. One or more of the plurality of time-varying acoustic parameters is modulated in accordance with at least the signal value of the time-domain signal (e.g., Time-Domain Signal 218, FIG. 2B, produced by Signal Conditioning Module 130). In some embodiments, synthesizer module (e.g., Synthesizer Module 150) combines the concurrently generated set of acoustic parameters to produce a representation of an acoustic signal corresponding to the time-domain signal (e.g., Time-Domain Signal 218, FIG. 2B, produced by Signal Conditioning Module 130).

FIG. 2A illustrates a block diagram of an analog front end (e.g., Analog Front End 120, FIG. 1) optionally included in Brain Interface System 100. In some embodiments, Analog Front End 120 receives a sensor time-domain signal (e.g., Sensor Time-Domain Signal 201) from a respective Sensor 110 and pre-processes the sensor time-domain signal to produce a filtered sensor time-domain signal (e.g., Filtered Sensor Time-Domain Signal 207). When Brain Interface System 100 includes a plurality of Analog Front Ends 120, the Analog Front Ends 120 process a corresponding number of sensor time-domain signals in parallel to produce filtered sensor time-domain signals.

In some embodiments, Analog Front End 120 includes interface circuitry (e.g., Interface Analog Circuitry 202) to interface with a respective Sensor 110, for example, by way of providing bias voltages and/or currents to the respective Sensor 110, buffering signals (e.g., using a buffer amplifier) received from Sensor(s) 110 and/or providing appropriate coupling conditions (e.g., providing appropriate input impedance) for interfacing with the signals received from Sensor(s) 110.

Alternatively, or in addition, according to some implementations, Analog Front End 120 includes one or more Amplifiers 204 and/or Filters 206 to pre-process (e.g., amplify and/or filter) sensor time-domain signals corresponding to brain electrical activity (e.g., Sensor Time-Domain Signal 201, FIG. 2A) obtained (e.g., sensed and/or acquired) from one or more Sensors 110. As noted above, in some embodiments, Analog Front End 120 produces a filtered sensor time-domain signal (e.g., Filtered Sensor Time-Domain Signal 207).

Figure 2B:
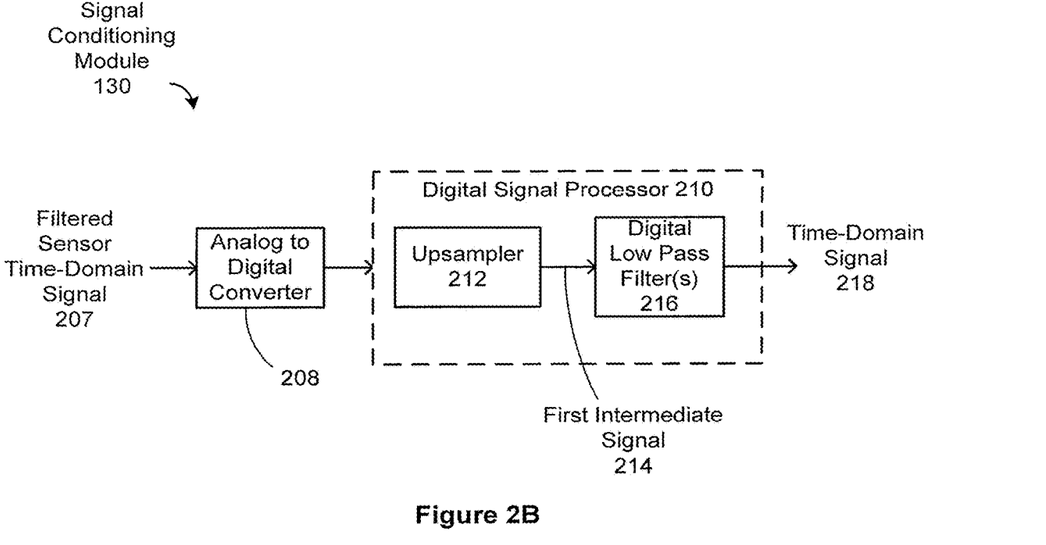
FIG. 2B is a block diagram illustrating a signal conditioning module used for processing electrical signals obtained from a human brain, in accordance with some embodiments.

FIG. 2B illustrates a block diagram of a signal conditioning module (e.g., Signal Conditioning Module 130) included in Brain Interface System 100. As shown in FIG. 2B, Signal Conditioning Module 130 receives filtered sensor time-domain signals (e.g., Filtered Sensor Time-Domain Signal 207)—optionally obtained after pre-processing by Analog Front End 120—and conditions the filtered sensor time-domain signals to produce time-domain signals (e.g., Time-Domain Signal 218).

In some embodiments, the signal conditioning module (e.g., Signal Conditioning Module 130) includes a data convertor (e.g., Analog to Digital Convertor 208) for converting an analog filtered sensor time-domain signal obtained from Sensor(s) 110 (optionally after pre-processing by Analog Front End 120) to a corresponding digital representation with a predefined sampling rate (e.g., a sampling rate between 500 Hz and 2 kHz, such as 500 Hz; or more generally a sampling rate between 400 Hz to 4 kHz). Signal Conditioning Module 130 includes an upsampler (e.g., Upsampler 212) to upsample (e.g., increase the sampling rate of) the digital representation of the analog filtered sensor time-domain signal to produce a first intermediate signal (e.g., First Intermediate Signal 214). In some embodiments, the digital representation of the analog filtered sensor time-domain signal is upsampled to produce a first intermediate signal having audio sampling rates, for example, sampling rates (e.g., 48 kHz) used in conventional audio applications. In some implementations, the first intermediate signal (e.g., First Intermediate Signal 214) produced by Upsampler 212 has a sampling rate of 48 kHz.

In some implementations, Signal Conditioning Module 130 includes one or more digital low-pass filters (e.g., Digital Low Pass Filter(s) 216) for filtering First Intermediate Signal 214 so as to produce Time-Domain Signal 218. In some implementations, Digital Low Pass Filter(s) 216 is a second order low-pass Butterworth filter with a 250 Hz corner frequency. Digital Low Pass Filter(s) 216 filter(s) First Intermediate Signal 214 to produce Time-Domain Signal 218. In some embodiments, Upsampler 212 and Digital Low Pass Filter(s) 216 are implemented in Digital Signal Processor 210, sometimes called a DSP. In some other implementations, Upsampler 212 and Digital Low Pass Filter(s) 216 are implemented in circuitry. Alternatively, Upsampler 212 and Digital Low Pass Filter(s) 216 are implemented in software executed by a general purpose processor. Without limitation, it is noted that upsampling and then low pass filtering the digital representation of the analog filtered sensor time-domain signal may be used to convert the output of one or more inter-cranial or extra-cranial sensors to a form that is suitable for use with a music or other audio synthesizer, while removing or limiting artifacts produces by the conversion process.

Figure 2C:
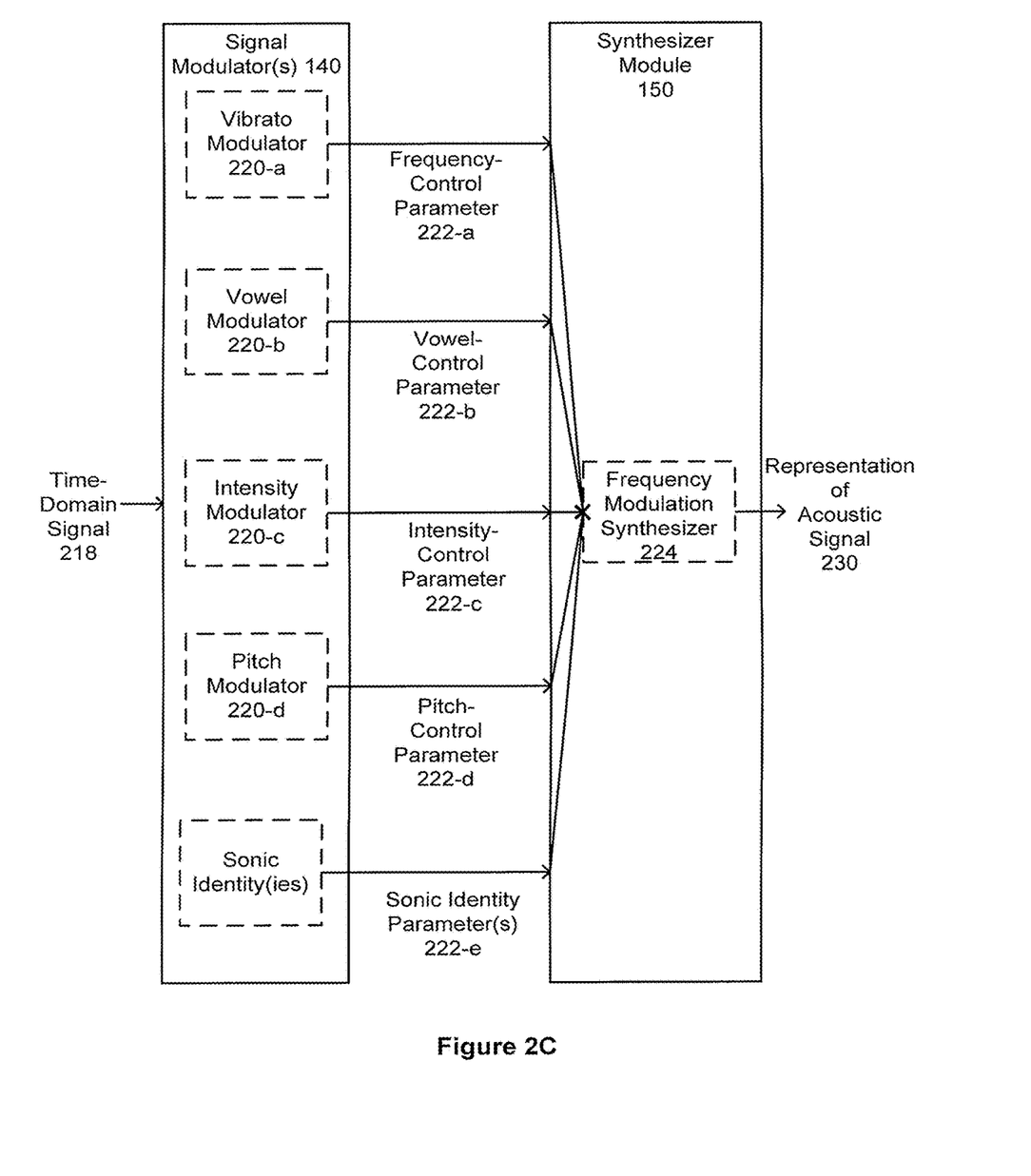
FIG. 2C is a block diagram illustrating signal modulators and a synthesizer module used for processing electrical time-domain signals obtained from a human brain to produce a representation of an acoustic signal, in accordance with some embodiments.

FIG. 2C illustrates a block diagram of Signal Modulators 140 and Synthesizer Module 150. Signal Modulators 140 receive Time-Domain Signal 218 from Signal Conditioning Module 130 (as explained above with reference to FIG. 2B). Signal Modulators 140 concurrently generate a set of acoustic parameters, including a plurality of time-varying acoustic parameters. In some embodiments, the plurality of acoustic parameters include a frequency-control parameter (e.g., Frequency-Control Parameter 222-$a$). In some embodiments, the plurality of acoustic parameters includes a vowel-control parameter (e.g., Vowel-Control Parameter 222-$b$). In some embodiments, the plurality of acoustic parameters includes a time-varying intensity-control parameter (e.g., Intensity-Control Parameter 222-$c$). In some embodiments, the set of acoustic parameters includes a pitch-control parameter (e.g., Pitch-Control Parameter 222-$d$). In some embodiments, the set of acoustic parameters includes one or more sonic identity parameters (e.g., Sonic Identity Parameter(s) 222-$e$).

In some embodiments, Signal Modulator(s) 140 include(s) a vibrato modulator (e.g., Vibrato Modulator 220-$a$) which generates a vibrato or frequency-control parameter (e.g., Frequency-Control Parameter 222-$a$). In some implementations, the vibrato modulator (e.g., Vibrato Modulator 220-$a$) obtains a base frequency or pitch (e.g., a base frequency such as 50 Hz, 100 Hz, or any suitable frequency in the range of 50 Hz to 4 kHz) and modulates the base frequency in accordance with the signal value (e.g., amplitude, intensity and/or power) of the time-domain signal (e.g., Time-Domain Signal 218). In other implementations, the vibrato modulator generates a vibrato or frequency-control parameter in accordance with the signal value of the time-domain signal (e.g., Time-Domain Signal 218) that does not incorporate the base frequency or pitch. The amount of vibrato, as represented by the vibrato or frequency-control parameter, controls variations in frequency in the synthesized audio signal (i.e., the representation of an acoustic signal corresponding to the time-domain signal).

In some embodiments, Signal Modulator(s) 140 include(s) a vowel modulator (e.g., Vowel Modulator 220-$b$) which generates a vowel-control parameter (e.g., Vowel-Control Parameter 222-$b$). In some implementations, a vowel modulator (e.g., Vowel Modulator 220-$b$) selects a sequence of acoustic waveform patterns from a set of N (e.g., N is an integer in the range of 2 to 15, such as N=12) acoustic waveform patterns comprising a sequence of phoneme waveform patterns (e.g., phoneme patterns corresponding to sounds in spoken language). In some implementations, the phoneme patterns include a plurality of vowel waveform patterns, and optionally include phoneme patterns (e.g., "sss" or "vvv") that are not vowel waveform patterns. In some implementations, each of the phoneme patterns is distinguished from the other phoneme waveform patterns in the set with respect to acoustic characteristics such as formants. In some embodiments, vowel modulator (e.g., Vowel Modulator 220-$b$) modulates a rate at which the acoustic waveform (e.g., vowel waveform) patterns are sequentially selected in accordance with the signal value (e.g., amplitude, intensity and/or power) of the time-domain signal. For example, vowel modulator (e.g., Vowel-Control Parameter 222-$b$) modulates a rate at which acoustic waveform patterns from a set of 12 acoustic waveform patterns are sequentially selected in accordance with the signal value (e.g., amplitude) of the time-domain signal (e.g., Time-Domain Signal 218). For example, an increase in signal value (e.g., amplitude) of the time-domain signal (e.g., Time-Domain Signal 218), causes vowel modulator (e.g., Vowel-Control Parameter 222-$b$) to sequentially select acoustic waveform patterns from a set of 12 acoustic waveform patterns more rapidly or at an increased rate; and conversely, a decrease in signal value (e.g., amplitude) of the time-domain signal (e.g., Time-Domain Signal 218), causes vowel modulator (e.g., Vowel-Control Parameter 222-$b$) to sequentially select acoustic waveform patterns from a set of 12 acoustic waveform patterns more gradually (e.g., slowly) or at a decreased rate.

In some embodiments, Signal Modulators 140 include an intensity modulator (e.g., Intensity Modulator 220-$c$) which generates an intensity-control parameter (e.g., Intensity-Control Parameter 222-$c$). For example, an intensity modulator (e.g., Intensity Modulator 220-$c$) computes a time-varying amplitude value in accordance with the signal value (e.g., amplitude, intensity and/or power) of the time-domain signal (e.g., Time-Domain Signal 218) and generates a time-varying intensity-control parameter (e.g., Intensity-Control Parameter 222-$c$) corresponding to the computed time-varying amplitude value. In some implementations, an increase in signal value (e.g., amplitude) of the time-domain signal (e.g., Time-Domain Signal 218), causes the time-varying amplitude value—and corresponding time-varying intensity-control parameter (e.g., Intensity-Control Parameter 222-$c$)—computed by intensity modulator (e.g., Intensity Modulator 220-$c$) to increase. Conversely, a decrease in signal value of the time-domain signal (e.g., Time-Domain Signal 218), causes the time-varying amplitude value—and corresponding time-varying intensity-control parameter (e.g., Intensity-Control Parameter 222-$c$)—computed by intensity modulator (e.g., Intensity Modulator 220-$c$) to decrease.

In some embodiments, Signal Modulator(s) 140 include(s) a pitch modulator (e.g., Pitch Modulator 220-$d$) which generates a pitch-control parameter (e.g., Pitch-Control Parameter 222-$d$). In some embodiments, pitch modulator (e.g., Pitch Modulator 220-$d$) selects a base frequency (e.g., corresponding to an acoustic pitch) in accordance with a spatial location of sensing the time-domain signal. In some embodiments, pitch modulator (e.g., Pitch Modulator 220-$d$) generates a time-varying pitch-control parameter in accordance with the selected base frequency and the signal value (e.g., amplitude, intensity and/or power) of the time-domain signal (e.g., Time-Domain Signal 218, FIG. 2B). For example, pitch modulator (e.g., Pitch Modulator 220-$d$) selects a base frequency (e.g., a pitch) in accordance with a spatial location in the brain of sensing (e.g., by way of Sensor(s) 110 located at different spatial locations in the brain) of the time-domain signal (e.g., Sensor Time-Domain Signal 201, FIG. 2A). For example, for a time-domain signal obtained from the left hemisphere in the brain, pitch modulator (e.g., Pitch Modulator 220-d) selects a lower base frequency (e.g., a frequency corresponding to the pitch of male voice); whereas for a time-domain signal obtained from the right hemisphere in the brain, pitch modulator (e.g., Pitch Modulator 220-d) selects a higher base frequency (e.g., a frequency corresponding to the pitch of female voice). More generally, in some implementations, when more than one time-domain signal is obtained from distinct intra-cranial sensors in the brain (or from distinct extra-cranial sensors), each time-domain signal is assigned a distinct base frequency so as to enable a listener to distinguish between the "voices" (acoustic signals or acoustic signal portions) corresponding to the distinct sensors and their time-domain signals.

In some embodiments, Signal Modulator(s) 140 generates, obtains or otherwise provides one or more sonic identity parameters 222-e. In some embodiments, Signal Modulator(s) 140 selects a sonic identity (for example, specific defining acoustic characteristics; e.g., acoustic characteristics associated with specific musical instruments) in accordance with a spatial location in the brain of sensing (e.g., by way of Sensor(s) 110 located at different spatial locations in the brain) and generates, obtains or otherwise provides one or more sonic identity parameter 222-e in accordance with the selected sonic identity. For example, for a time-domain signal obtained from the left hemisphere in the brain, Signal Modulator(s) 140 selects a sonic identity corresponding to the sonic identity of (e.g., acoustic characteristics defining or associated with) a violin; whereas for a time-domain signal obtained from the right hemisphere in the brain, Signal Modulator(s) 140 selects a sonic identity corresponding to the sonic identity of (e.g., acoustic characteristics defining or associated with) a guitar. More generally, in some implementations, when more than one time-domain signal is obtained from distinct intra-cranial sensors in the brain (or from distinct extra-cranial sensors), each time-domain signal is assigned a distinct sonic identity (e.g., and a corresponding set of one or more sonic identity parameters 222-e), so as to enable a listener to distinguish between the "voices" (acoustic signals or acoustic signal portions) corresponding to the distinct sensors and their time-domain signals.

One or more of the plurality of time-varying acoustic parameters (e.g., Frequency-Control Parameter 222-a, Vowel-Control Parameter 222-b, and/or Intensity-Control Parameter 222-c) is modulated in accordance with at least the signal value (e.g., amplitude, intensity, and/or power) of the time-domain signal (e.g., Time-Domain Signal 218, FIG. 2B, produced by Signal Conditioning Module 130).

A synthesizer module (e.g., Synthesizer Module 150) combines the concurrently generated set of acoustic parameters (e.g., the acoustic parameters produced by Signal Modulator(s) 140 described above) to produce a representation of an acoustic signal (e.g., Representation of Acoustic Signal 230) corresponding to the time-domain signal (e.g., Time-Domain Signal 218, FIG. 2B, produced by Signal Conditioning Module 130). In some embodiments, Synthesizer Module 150 is a music synthesizer or a music synthesizer module, for example a frequency modulation synthesizer (e.g., Frequency Modulation Synthesizer 224). In some embodiments, a frequency modulation synthesizer (e.g., Frequency Modulation Synthesizer 224) uses frequency modulation synthesis, controlled by the concurrently generated set of acoustic parameters, to generate a representation of an acoustic signal 230. For example, the frequency modulation synthesizer (e.g., Frequency Modulation Synthesizer 224) modifies the timbre (e.g., the quality) of a waveform by frequency modulating it with a modulating signal. With respect to frequency modulation synthesis, U.S. Pat. No. 4,018,121, "Method of synthesizing a musical sound" is hereby incorporated by reference as background information.

As shown in FIG. 1, in some embodiments, Signal Modulator 140 and/or Synthesizer Module 150 are implemented in Digital Processor 160. In some implementations, Signal Modulator 140 and/or Synthesizer Module 150 are implemented in a digital signal processor, sometimes called a DSP. In some implementations, Signal Modulator 140 and/or Synthesizer Module 150 are implemented in circuitry. And in some implementations, Signal Modulator 140 and/or Synthesizer Module 150 are implemented in software executed by a general-purpose processor.

Figure 3:
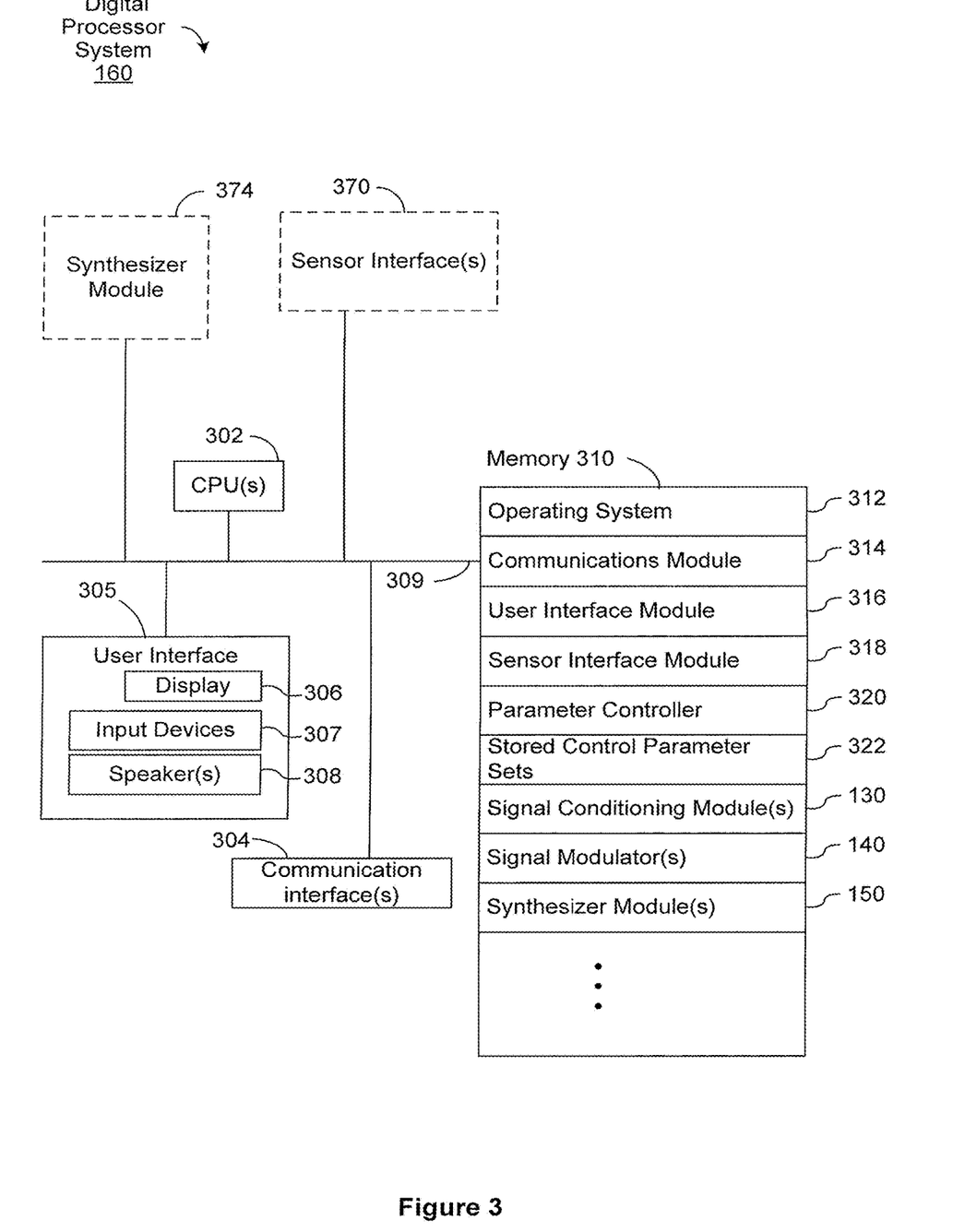
FIG. 3 is a block diagram illustrating a digital processor used for processing signals representing brain activity, in accordance with some embodiments.

FIG. 3 is a block diagram illustrating Digital Processor System 160 in accordance with some embodiments. Digital Processor System 160 typically includes one or more processing units (CPU's) 302 for executing modules, programs and/or instructions stored in Memory 310 and thereby performing processing operations; one or more network or other Communications Interfaces 304; Memory 310; and one or more Communication Buses 309 for interconnecting these components. The Communication Buses 309 optionally include circuitry (sometimes called a chipset) that interconnects and controls communications between system components. Digital Processor System 160 optionally includes a User Interface 305 comprising a Display 306, one or more Input Devices 307 (e.g., keyboard, mouse, touch screen, keypads, etc.), and Speaker(s) 308 (optionally for audio playback of acoustic signals corresponding to brain activity). Digital Processor System 160 optionally includes Sensor Interface(s) 370 for interfacing with Sensor(s) 110 (FIG. 1) and/or Analog Front End 120 (FIG. 1) and Synthesizer Module 374 for combining concurrently generated acoustic parameters to produce a representation of an acoustic signal (e.g., Representation of Acoustic Signal 230, FIG. 2C) corresponding to one or more time-domain signals (e.g., Time-Domain Signal 218, FIG. 2B).

Memory 310 includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. Memory 310 optionally includes one or more storage devices remotely located from the CPU(s) 302. Memory 310, or alternately the non-volatile memory device(s) within memory 310, comprises a non-transitory computer readable storage medium. In some embodiments, Memory 310, or the computer readable storage medium of Memory 310 stores the following programs, modules and data structures, or a subset thereof:

Operating System 312 that includes procedures for handling various basic system services and for performing hardware dependent tasks;

Network Communication Module 314 that is used for connecting Digital Processor 160 to other computers via the one or more communication network interfaces 309 (wired or wireless) and one or more communication networks, such as the Internet, other wide area networks, local area networks, metropolitan area networks, and so on;

User Interface Module 316 that receives commands from the user via one or more Input Devices 307 of User Interface 305, generates user interface objects in Display Device 306, and optionally generates representations of signals corresponding to brain activity, information corresponding to sensor(s) and sensor interfaces, and information related to the configuration of Brain Interface System 100 for display on Display Device 306;

Parameter Controller 320 that controls (e.g., executes instructions for) the generation of the set of acoustic parameters, including a plurality of time-varying acoustic parameters (such as a frequency-control parameter (sometimes called a vibrato parameter), a vowel-control parameter, an intensity-control parameter, a pitch-control parameter, and/or an identity-control parameter). Parameter Controller 320 also interacts with Sensor Interface(s) 370 to facilitate selection of parameters (e.g., any of the aforementioned parameters) and corresponding parameter values based on the sensor(s) selected and sensor signals obtained (e.g., based on a spatial location in the brain of sensing the time-domain signal). For example, Sensor Interface Module 318 interfaces with Parameter Controller 320 to communicate a set of parameters, corresponding to one or more of pitch, vowel selection, vibrato, intensity (amplitude), and sonic identity parameter, selected in accordance the selected sensor, or in accordance with a spatial location in the brain of sensing a time-domain signal;

Stored Control Parameter Sets 322 that include one or more sets of signal parameters or values corresponding to signal parameters (for example, one or more values of base frequencies, a set of acoustic waveform patterns corresponding to phoneme patterns, one or more sonic identities etc.);

Signal Conditioning Module(s) 130 upsamples and low pass filters the sensor time-domain signal to produce a time-domain signal representing brain activity;

Signal Modulator(s) 140 concurrently generate(s) a set of acoustic parameters, including a plurality of time-varying acoustic parameters, for example, a frequency-control parameter (e.g., Frequency-Control Parameter 222-a, FIG. 2C), a vowel-control parameter (e.g., Vowel-Control Parameter 222-b, FIG. 2C), a time-varying intensity-control parameter (e.g., Intensity-Control Parameter 222-c, FIG. 2C), a pitch-control parameter (e.g., Pitch-Control Parameter 222-d, FIG. 2C), and/or an sonic identity parameter (e.g., Sonic Identity Parameter(s) 222-e, FIG. 2C); and Synthesizer Module(s) 150 combines the concurrently generated set of acoustic parameters to produce a representation of an acoustic signal (e.g., Representation of Acoustic Signal 230, FIG. 2C) corresponding to the time-domain signal (e.g., Time-Domain Signal 218, FIG. 2B, produced by Signal Conditioning Module 130).

Each of the above identified elements is optionally stored in one or more of the previously mentioned memory devices of Digital Processor System 160, and corresponds to a set of instructions for performing a function described above.

The above identified modules or programs (i.e., sets of instructions) need not be implemented as separate software programs, procedures or modules, and thus various subsets of these modules is optionally combined or otherwise rearranged in various embodiments. In some embodiments, Memory 310 optionally stores a subset of the modules and data structures identified above. Furthermore, Memory 310 optionally stores additional modules and data structures not described above.

Although FIG. 3 shows "Digital Processor System 160," FIG. 3 is intended more as functional description of the various features which are optionally present in a digital processor system than as a structural schematic of the embodiments described herein. In practice, and as recognized by those of ordinary skill in the art, items shown separately could be combined and some items could be separated. For example, some items shown separately in FIG. 3 could be implemented on a single digital processor system and single items could be implemented by one or more digital processor systems. The actual number of digital processor systems used to implement Digital Processor System 160 and how features are allocated among them will vary from one implementation to another.

Figure 4A:
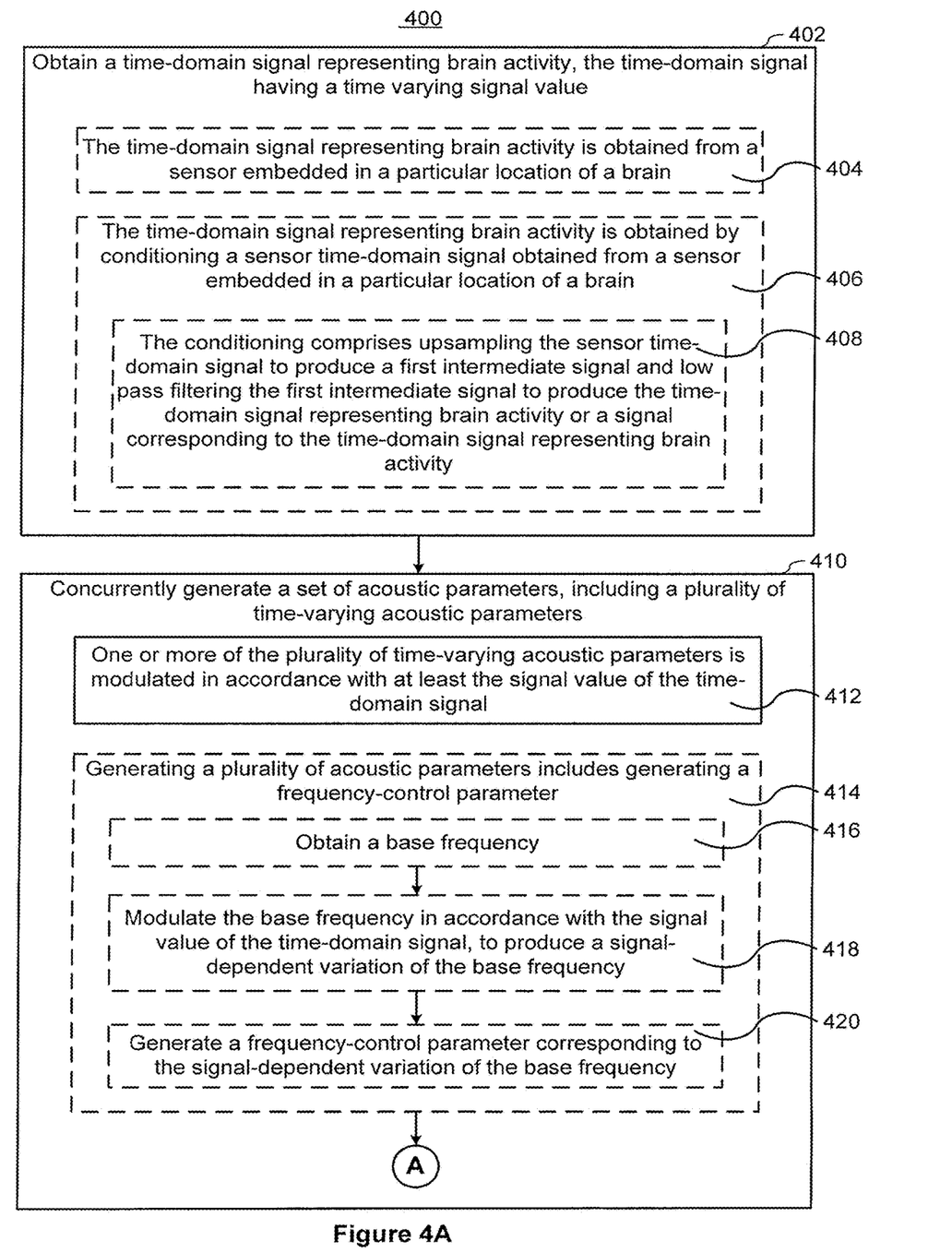
FIGS. 4A-4C include a flow chart illustrating a method for sonifying brain electrical activity, in accordance with some embodiments.
Figure 4B:
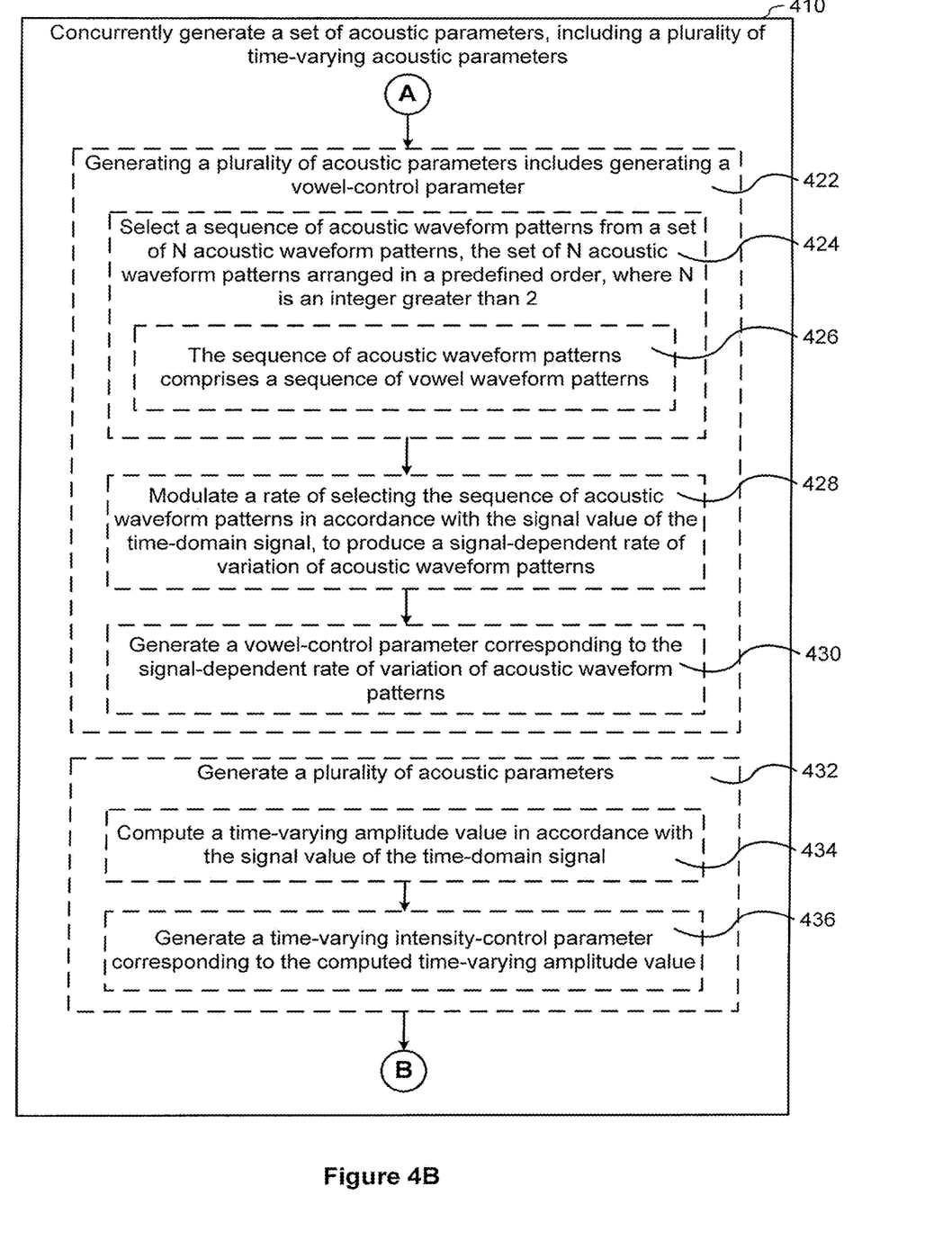
Figure 4C:
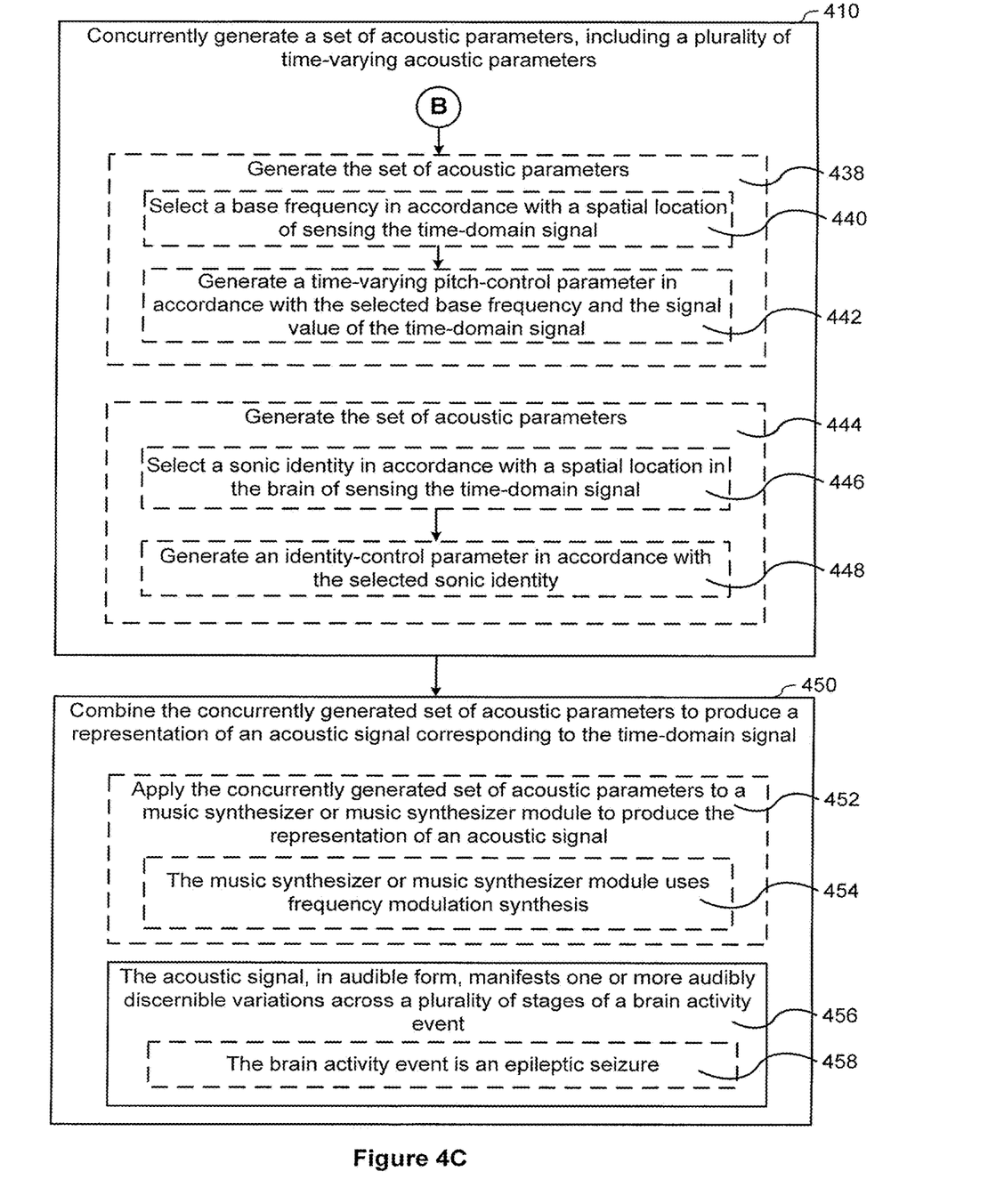

FIG. 4 is a flowchart representing method 400 for sonifying brain electrical activity, according to certain embodiments of the invention. Method 400 is optionally governed by instructions that are stored in a computer readable storage medium and that are executed by a digital processor system (or, optionally, one or more digital processor systems) (e.g., Digital Processor 160). Each of the operations shown in FIG. 4 optionally corresponds to instructions stored in a computer memory or computer readable storage medium. The computer readable storage medium optionally includes a magnetic or optical disk storage device, solid state storage devices such as flash memory, or other non-volatile memory device or devices. The computer readable instructions stored on the computer readable storage medium are in source code, assembly language code, object code, or other instruction format that is interpreted by one or more processors.

The digital processor system obtains (402) a time-domain signal (e.g., Time-Domain Signal 218, FIG. 2B) representing brain activity, the time-domain signal having a time varying signal value. In some embodiments, the time-domain signal representing brain activity is obtained (404) from a sensor embedded in a particular location of a brain. For example, as explained with reference to FIG. 1 and FIG. 2B, Time-Domain Signal 218 (FIG. 2B) is obtained from Sensor(s) 110 embedded in a particular location of a brain (e.g., Intra-cranial Sensor 110-2). In some implementations, Intra-cranial Sensor 110-2 is formed (e.g., fabricated) on a needle embedded in the brain with one or more sensing elements located along the length and/or circumference of the needle and differential voltages (e.g., differences in voltage values) are measured between two measurement locations (e.g., between two sensing elements) to produce a differential voltage signal corresponding optionally to Sensor Time-Domain Signal 201, FIG. 2A or to Time-Domain Signal 218, FIG. 2B.

In some embodiments, the time-domain signal representing brain activity is obtained (406) by conditioning a sensor time-domain signal obtained from a sensor embedded in a particular location of a brain. For example, as shown in FIG. 1 and FIGS. 2A-2B, Sensor Time-Domain Signal 201 is obtained from a sensor embedded in a particular location of a brain (e.g., from Intra-cranial Sensor 110-2, FIG. 1) and—after optionally being pre-processed by Analog Front End 120 to produce Filtered Sensor Time-Domain Signal 207—is conditioned by Signal Conditioning Module 130.

In some embodiments, the conditioning comprises (408) upsampling the sensor time-domain signal to produce a first intermediate signal and low pass filtering the first intermediate signal to produce the time-domain signal representing brain activity or a signal corresponding to the time-domain signal representing brain activity. For example, as shown in FIG. 2B, Filtered Sensor Time-Domain Signal 207—after conversion from an analog signal to a corresponding digital signal—is upsampled (e.g., by Upsampler 212, FIG. 2B) to produce a first intermediate signal (e.g., First Intermediate Signal 214, FIG. 2B). For example, as explained above, if the original sampling rate of the digital representation of the analog filtered sensor time-domain signal corresponds to 500 Hz, the first intermediate signal (e.g., First Intermediate Signal 214) produced by Upsampler 212 has a sampling rate used in conventional audio applications (e.g., 48 kHz). First Intermediate Signal 214 is then low pass filtered (e.g., by Digital Low Pass Filter(s) 216, FIG. 2B) to produce the time-domain signal representing brain activity or a signal corresponding to the time-domain signal representing brain activity (e.g., Time-Domain Signal 218, FIG. 2B).

The digital processor system concurrently generates (410) a set of acoustic parameters (e.g., see operations 412-448), including a plurality of time-varying acoustic parameters. In this context, parameters are "concurrently generated" even if they are literally generated serially by single-threaded processor, when the resulting parameters are used or applied concurrently for generating an audio signal, or a representation of an audio signal. Typically, two or more concurrently generated parameters are generated or updated in response to a stream of digital signal values corresponding to the time-domain signal.

One or more of the plurality of time-varying acoustic parameters is modulated (412) in accordance with at least the signal value of the time-domain signal. For example, as explained above with reference to FIG. 2C, Signal Modulator(s) 140 (optionally included in Digital Processor 160) concurrently generate(s) a set of acoustic parameters, including a plurality of time-varying acoustic parameters. In some embodiments, as described in relation to FIG. 2C above, the plurality of acoustic parameters includes a vibrato or frequency-control parameter (e.g., Frequency-Control Parameter 222-a), a vowel-control parameter (e.g., Vowel-Control Parameter 222-b), and/or a time-varying amplitude or intensity-control parameter (e.g., Intensity-Control Parameter 222-c). In some embodiments, the set of acoustic parameters includes a pitch-control parameter (e.g., Pitch-Control Parameter 222-d) and/or an sonic identity parameter (e.g., Sonic Identity Parameter 222-e).

In some embodiments, generating a plurality of acoustic parameters includes (414) generating a vibrato or frequency-control parameter (as described herein with respect to operations 416-420). For example, as described above with reference to FIG. 2C, Signal Modulator(s) 140 (optionally included in a digital processor system) includes Vibrato Modulator 220-a, which generates Frequency-Control Parameter 222-a.

In some embodiments, the digital processor system obtains (416) a base frequency. In some embodiments, the digital processor system modulates (418) the base frequency in accordance with the signal value of the time-domain signal, to produce a signal-dependent variation of the base frequency. In some embodiments, the digital processor system generates (420) a frequency-control parameter corresponding to the signal-dependent variation of the base frequency. For example, as explained above, vibrato modulator (e.g., Vibrato Modulator 220-a, FIG. 2C) generates a control parameter for controlling the amount of vibrato (which can be considered to be the amount of frequency variation) produced by a music or audio synthesizer. In some implementations (e.g., implementations in which pitch and vibrato are controlled during audio synthesis by separate parameters) the frequency-control parameter is independent of the base frequency or pitch, while in other implementations the frequency-control parameter incorporates the base frequency or pitch.

In some embodiments, generating a plurality of acoustic parameters includes (422) generating a vowel-control parameter (as described herein with respect to operations 424-430). For example, as shown in FIG. 2C, Signal Modulator(s) 140 (optionally included in Digital Processor 160) comprise(s) Vowel Modulator 220-b which generates Vowel-Control Parameter 222-b.

In some embodiments, Digital Processor (e.g., Digital Processor 160) sequentially selects (424) acoustic waveform patterns from a ordered set of N acoustic waveform patterns, the set of N acoustic waveform patterns arranged in a predefined order, where N is an integer greater than 2. In some embodiments, the sequence of selected acoustic waveform patterns comprises (426) a sequence of vowel waveform patterns. In some embodiments, Digital Processor (e.g., Digital Processor 160) modulates (428) a rate of sequentially selecting acoustic waveform patterns in accordance with the signal value of the time-domain signal, to produce a signal-dependent rate of variation of acoustic waveform patterns. In some embodiments, Digital Processor (e.g., Digital Processor 160) generates (430) a vowel-control parameter corresponding to the signal-dependent rate of variation of acoustic waveform patterns.

For example, as described above, vowel modulator (e.g., Vowel-Control Parameter 222-b) modulates a rate of sequentially selecting acoustic waveform patterns from a set of 12 acoustic waveform patterns in accordance with the signal value of the time-domain signal (e.g., Time-Domain Signal 218, FIG. 2C). For example, for an increase in signal value of the time-domain signal (e.g., Time-Domain Signal 218), vowel modulator (e.g., Vowel-Control Parameter 222-b) selects (e.g., scans through) a sequence of acoustic waveform patterns from a set of 12 acoustic waveform patterns more rapidly or at an increased rate; conversely, for a decrease in signal value of the time-domain signal (e.g., Time-Domain Signal 218), vowel modulator (e.g., Vowel-Control Parameter 222-b) selects (e.g., scans through) a sequence of acoustic waveform patterns from a set of 12 acoustic waveform patterns more gradually (e.g., slowly) or at a decreased rate.

In some embodiments, the digital processor system generates (432) a plurality of acoustic parameters, as described herein with respect to operations 434-436. In some embodiments, the digital processor system computes (434) a time-varying amplitude value in accordance with the signal value of the time-domain signal. In some embodiments, the digital processor system generates (436) a time-varying intensity-control parameter corresponding to the computed time-varying amplitude value.

For example, as described above in relation to FIG. 2C, an intensity modulator (e.g., Intensity Modulator 220-c, FIG. 2C) computes a time-varying amplitude value in accordance with the signal value of the time-domain signal (e.g., Time-Domain Signal 218, FIG. 2C) and generates a time-varying intensity-control parameter (e.g., Intensity-Control Parameter 222-c, FIG. 2C) corresponding to the computed time-varying amplitude value. In some implementations, for an increase in signal value of the time-domain signal (e.g., Time-Domain Signal 218), the time-varying amplitude value—and corresponding time-varying intensity-control parameter (e.g., Intensity-Control Parameter 222-c)—computed by intensity modulator (e.g., Intensity Modulator 220-c) increases. Conversely, for a decrease in signal value of the time-domain signal (e.g., Time-Domain Signal 218), the time-varying amplitude value—and corresponding time-varying intensity-control parameter (e.g., Intensity-Control Parameter 222-*c*)—computed by intensity modulator (e.g., Intensity Modulator 220-*c*) decreases.

In some embodiments, the digital processor system generates (438) the set of acoustic parameters, as described herein with respect to operations 440-442. In some embodiments, the digital processor system selects (440) a base frequency in accordance with a spatial location of sensing the time-domain signal. In some embodiments, the digital processor system generates (442) a time-varying pitch-control parameter in accordance with the signal value of the time-domain signal, and optionally in accordance with the selected base frequency. For example, as shown in FIG. 2C, Signal Modulator(s) 140 (optionally included in Digital Processor 160) comprise(s) Pitch Modulator 220-*d* which generates Pitch-Control Parameter 222-*d* in accordance a signal value of the time-domain signal (e.g., Time-Domain Signal 218), and optionally in accordance with a selected base frequency (e.g., corresponding to a spatial location of sensing the time-domain signal).

Without limitation with respect to other implementations, in some implementations the set of acoustic parameters are generated, in accordance with a set of instructions executed by one or more processors of a digital processor system, as described above. The following is an example of a pseudo-code representation of instructions for generating the set of acoustic parameters, once per time period (e.g., once every 10 milliseconds), where SigVal is the signal value for the current time period:

```
// amplitude amplitude.param = max(0.0, c1 + c2*SigVal);
//pitch pitch.param = ConvertMidiToFreq(c3 - c4*SigVal);
// vibrato vibrato-gain.param = pitch.param * (2.sup.c5 - 1);
vibrato.param = vibrato.param + c6*SigVal; vibrato.freq.param =
max(0.0, min(c7, c8+vibrato.param));
//vowel vow = vow + (c9 * SigVal); vowel.param = integer
( abs(vow) ) modulo
12;
``` where, in one example, the following coefficient values are used: c1=0.1, c2=20, c3=45, c4=5, c5=0.05, c6=4, c7=8.0, c8=4.5, c9=20. Further, "ConvertMidiToFreq" is a function for converting a midi note to a frequency value, "max" is a function that outputs the maximum of its input values, "min" is a function that outputs the minimum of its input values, "abs" is a function that outputs the absolute value of its input, and "integer" is a function that outputs the integer portion of its input. In another example, in which two or more multiple time-domain signals are processed to produce a corresponding number of audio signals (sometimes called voices for ease of reference), one or more of the coefficients (e.g., c1 to c9 in the above example) are different for different ones of the audio signals, thereby producing audio signals that are audibly distinct. In one example, coefficients c3 (corresponding to base frequency) and c6 (corresponding to amount of vibrato) and c9 (corresponding to rate at which the audio signal traverses a sequence of vowels or phonemes), have different values for each audio signal.

For example, as shown in FIG. 1, Sensor(s) 110 are located at different spatial locations in the brain for sensing the time-domain signal (e.g., Sensor Time-Domain Signal 201), and a base frequency (e.g., a pitch) is selected in accordance with a spatial location in the brain of sensing the time-domain signal. In this example, for a time-domain signal obtained from the left hemisphere in the brain, a lower base frequency (e.g., a frequency corresponding to the pitch of male voice) is selected; whereas for a time-domain signal obtained from the right hemisphere in the brain, a higher base frequency (e.g., a frequency corresponding to the pitch of female voice) is selected.

In some embodiments, the digital processor system generates (444) the set of acoustic parameters, as described with respect to operations 446-448. In some embodiments, the digital processor system selects (446) a sonic identity in accordance with a spatial location in the brain (or, alternatively, on the surface of the cranium) of sensing the time-domain signal. In some embodiments, the digital processor system generates (448) an identity-control parameter in accordance with the selected sonic identity. For example, as shown in FIG. 2C, Signal Modulator(s) 140 (optionally included in Digital Processor 160) comprise(s) Sonic Identity Modulator 220-*e* which generates Sonic Identity Parameter(s) 222-*e* in accordance with a selected sonic identity corresponding to a spatial location in the brain of sensing the time-domain signal.

For example, as shown in FIG. 1, Sensor(s) 110 are located at different spatial locations in the brain for sensing the time-domain signal (e.g., Sensor Time-Domain Signal 201), and a sonic identity is selected in accordance with a spatial location in the brain (or, alternatively, on the surface of the cranium) of sensing the time-domain signal. In this example, for a time-domain signal obtained from the left hemisphere in the brain, a sonic identity is selected corresponding to the sonic identity of (e.g., acoustic characteristics defining or associated with) a violin (or a first "voice"); whereas for a time-domain signal obtained from the right hemisphere in the brain, a sonic identity is selected corresponding to the sonic identity of (e.g., acoustic characteristics defining or associated with) a guitar (or as second "voice"). In some implementations, the sonic identity is simply the base frequency of each generated acoustic signal (or representation of an acoustic signal), while in some other implementations, the sonic identity determines both the base frequency and one or more parameters (e.g., multipliers, offsets, etc.) that are used while generating the acoustic parameters corresponding to each time-domain signal (e.g., corresponding to each sensor signal being sonified).

The digital processor system combines (450) the concurrently generated set of acoustic parameters to produce a representation of an acoustic signal corresponding to the time-domain signal. For example, as shown in FIG. 2C, Synthesizer Module 150 (optionally included in Digital Processor 160) combines the concurrently generated set of acoustic parameters generated by Signal Modulator(s) 140 to produce a representation of an acoustic signal (Representation of Acoustic Signal 230) corresponding to the time-domain signal (e.g., Time-Domain Signal 218).

In some embodiments, the digital processor system applies (452) the concurrently generated set of acoustic parameters to a music synthesizer or music synthesizer module to produce the representation of an acoustic signal. In some embodiments, the music synthesizer or music synthesizer module uses (454) frequency modulation synthesis. For example, as shown in FIG. 2C, Synthesizer Module 150 uses frequency modulation synthesis implemented on Frequency Modulation Synthesizer 224.

The acoustic signal, in audible form, manifests (456) one or more audibly discernible variations across a plurality of stages of a brain activity event. In some embodiments, the brain activity event is (458) an epileptic seizure. For example, the acoustic signal corresponding to Representation of Acoustic Signal 230, in audible form, manifests one or more audibly discernible variations (e.g., variations in vibrato, in rate of change of vowel, and/or in intensity) across a plurality of stages of a brain activity event. In some embodiments in which the brain activity event is an epileptic seizure, the acoustic signal in audible form manifests one or more audibly discernible variations (change in volume, pitch, rate of vowel change) across the stages (e.g., normal state, pre-ictal phase, seizure phase and post-ictal phase) of the epileptic seizure. For example, the acoustic signal is periodic and has higher amplitude during the seizure phase, and is chaotic (has lower or little periodicity) and has lower amplitude during the normal state.

In some implementations, the brain activity event for which brain electrical signals are sonified is not an epileptic seizure, and instead is a respective brain activity event that is the subject of analysis or monitoring. For example, in some implementations the brain activity event for which brain electrical signals are sonified comprises brain activity while the human subject performs various tasks (e.g., mental tasks, physical tasks, operating an apparatus, answering questions, playing a musical instrument, taking an exam, performing or attempting to perform multiple tasks or functions concurrently, etc.), brain activity associated with experiencing various external stimuli, brain activity associated with physiological functions, brain activity associated with various diseases, and the like.

Figure 5:
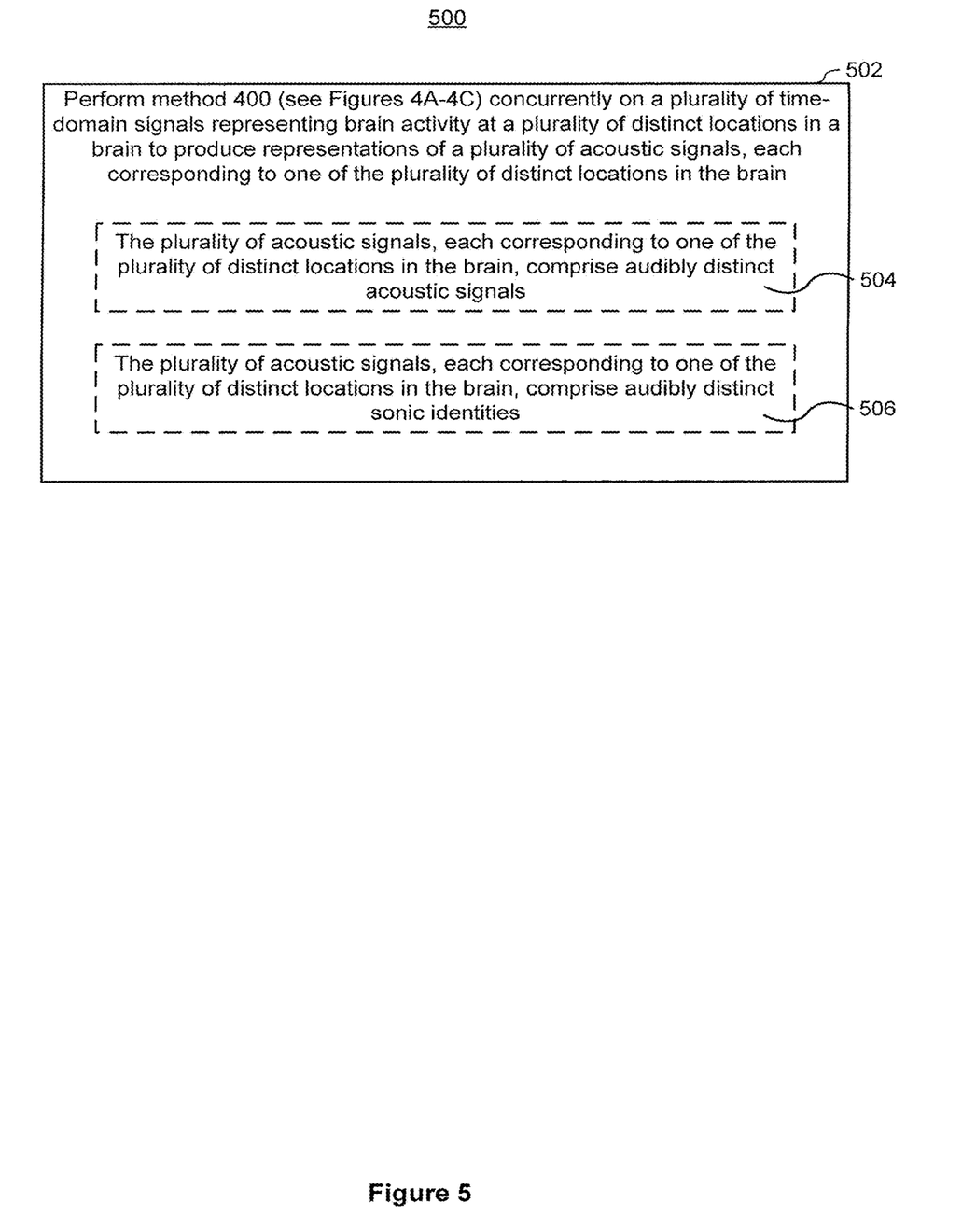
FIG. 5 includes a flow chart illustrating a method for sonifying brain electrical signals concurrently obtained from a plurality of distinct locations in the brain, in accordance with some embodiments.

FIG. 5 is a flowchart representing method 500 for sonifying brain electrical signals concurrently obtained from a plurality of distinct locations in the brain, according to certain embodiments of the invention. Method 500 is optionally governed by instructions that are stored in a computer readable storage medium and that are executed by one or more processors of one or more digital processor systems. Each of the operations shown in FIG. 5 optionally corresponds to instructions stored in a computer memory or computer readable storage medium. The computer readable storage medium optionally includes a magnetic or optical disk storage device, solid state storage devices such as Flash memory, or other non-volatile memory device or devices. The computer readable instructions stored on the computer readable storage medium are in source code, assembly language code, object code, or other instruction format that is interpreted by one or more processors.

In some implementations, the digital processor system (e.g., Digital Processor 160, FIG. 1 and FIG. 3) performs (502) method 400 (described herein with reference to FIGS. 4A-4C) concurrently on a plurality of time-domain signals representing brain activity at a plurality of distinct locations in a brain to produce representations of a plurality of acoustic signals, each corresponding to one of the plurality of distinct locations in the brain. For example, as shown in FIG. 1, Digital Processor 160 (FIG. 1 and FIG. 3) performs the above-described method 400 concurrently on a plurality of time-domain signals (e.g., a plurality of Sensor Time-Domain Signal(s) 201, FIG. 2C, obtained from a plurality of Sensor(s) 110, FIG. 1) representing brain activity at a plurality of distinct locations in a brain to produce representations of a plurality of acoustic signals (e.g., a plurality of Representation of Acoustic Signal 230, FIG. 2C). In some embodiments, Sensor(s) 110 (e.g., Intra-cranial Sensor 110-2), FIG. 1 include intracranial depth electrodes implanted in the brain at a plurality of locations to monitor electrical activity in the brain at the plurality of locations. In such implementations, the observed signal (e.g., Sensor Time-Domain Signal 201, FIG. 2A) obtained from each of Sensor(s) 110 (e.g., Intra-cranial Sensor 110-2) represents the aggregate activity (e.g., corresponding to 10,000 neurons) in the region proximate to the respective sensor (e.g., Intra-cranial Sensor 110-2). In some embodiments, arrays of sensors (e.g., Sensor(s) 110) are designed to produce a plurality of sensor time-domain signals (e.g., Sensor Time-Domain Signal 201, FIG. 2A). In such embodiments, each of the plurality of time-domain signals is normalized (e.g., normalized with respect to signal amplitude or power) and/or offset (e.g., by the addition or subtraction of a fixed signal value) relative to other time-domain signals in the plurality of time-domain signals. Statistical features of the plurality of time-domain signals, for example, obtained from arrays of sensors (e.g., Sensor(s) 110) are optionally used to enhance acoustic characteristics of the representations of a plurality of acoustic signals. For example, in some embodiments, an estimate of the "busiest" signal(s) (e.g., signals with the highest signal content) of the plurality of time domain signals (e.g., obtained from arrays of sensors (e.g., Sensor(s) 110) at a plurality of distinct locations in a brain) is computed based on activity detected or computed using a sliding window Fourier Transform. In such embodiments, the "busiest" signal(s) are used for method 400 (described herein with reference to FIGS. 4A-4C).

In some embodiments, the plurality of acoustic signals, each corresponding to one of the plurality of distinct locations in the brain (or, alternatively, to a particular sensor or set of sensors 110), comprise (504) audibly distinct acoustic signals. For example, the plurality of acoustic signals, each corresponding to one of the plurality of distinct locations in the brain, comprise audibly distinct pitch (e.g., base frequencies), different rates of vowel transition, different vibrato modulations, and/or different acoustic signal intensities (e.g., loudness of the acoustic signal). In some embodiments, the plurality of acoustic signals, each corresponding to one of the plurality of distinct locations in the brain, comprise (506) audibly distinct sonic identities. For example, as explained above, for a time-domain signal obtained from the left hemisphere in the brain, a sonic identity is selected corresponding to the sonic identity of (e.g., acoustic characteristics defining or associated with) a violin (or, more generally, a first "voice"); whereas for a time-domain signal obtained from the right hemisphere in the brain, a sonic identity is selected corresponding to the sonic identity of (e.g., acoustic characteristics defining or associated with) a guitar (or, more generally, a second "voice").

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method of sonifying brain signals using a digital processor system that comprises at least one processing unit, the method comprising:

generating, using the digital processor system, a plurality of continuously time-varying acoustic parameters from a continuous time-domain signal representing brain activity of a subject, the plurality of continuously time-varying acoustic parameters including a vowel-control parameter, an intensity-control parameter, and a pitch-control parameter, wherein at least three of the parameters in the plurality of continuously time-varying acoustic parameters are continuously modulated in proportion with at least the continuous time varying signal value of the time-domain signal during concurrent generation;

driving, with the digital processor system, an audio synthesizer using the generated plurality of continuously time-varying acoustic parameters to produce a representation of an acoustic signal corresponding to the brain activity of the subject represented by the continuous time-domain signal;

performing continuous audio playback of the representation of the acoustic signal using the digital processor system, wherein performing the continuous audio playback comprises audibly providing, with at least one speaker, the representation of the acoustic signal.

2. The method of claim 1, wherein the continuous time-domain signal representing brain activity of the subject is obtained from at least one sensor and the at least one sensor is affixed externally to the subject.

3. The method of claim 1, wherein the method is concurrently performed on a plurality of continuous time-domain signals representing brain activity at a plurality of distinct locations in a brain of the subject to produce representations of a plurality of acoustic signals, each corresponding to one of the plurality of distinct locations in the brain.

4. The method of claim 3, wherein the plurality of acoustic signals, each corresponding to one of the plurality of distinct locations in the brain, comprise audibly distinct acoustic signals.

5. The method of claim 3, wherein the plurality of acoustic signals, each corresponding to one of the plurality of distinct locations in the brain, comprise audibly distinct sonic identities.

6. The method of claim 1 wherein the audio synthesizer comprises a voice synthesizer, and wherein driving the audio synthesizer to produce the representation of the acoustic signal corresponding to the brain activity of the subject comprises utilizing the voice synthesizer to produce the representation of an acoustic signal.

7. The method of claim 6, wherein the voice synthesizer uses frequency modulation synthesis.

8. The method of claim 1, wherein generating the plurality of continuously time-varying acoustic parameters further comprises:
generating a frequency-control parameter in proportion with the time varying signal value of the continuous time-domain signal.

9. The method of claim 1, wherein generating the plurality of continuously time-varying acoustic parameters includes generating a frequency-control parameter by:
obtaining a base frequency or pitch;
modulating the base frequency or pitch in proportion with the signal value of the continuous time-domain signal, to produce a signal-dependent variation of the base frequency; and
generating the frequency-control parameter corresponding to the signal-dependent variation of the base frequency, and
wherein the audio synthesizer is further driven using the frequency-control parameter to produce the representation of the acoustic signal corresponding to the brain activity of the subject.

10. The method of claim 1, wherein generating the plurality of continuously time-varying acoustic parameters includes generating the vowel-control parameter by:

selecting a sequence of acoustic waveform patterns from a set of N acoustic waveform patterns, the set of N acoustic waveform patterns arranged in a predefined order, where N is an integer valuing at least 2;
modulating a rate of selecting the sequence of acoustic waveform patterns in proportion with the time varying signal value of the continuous time-domain signal, to produce a signal-dependent rate of variation of acoustic waveform patterns; and
generating the vowel-control parameter corresponding to the signal-dependent rate of variation of acoustic waveform patterns.

11. The method of claim 10, wherein the sequence of acoustic waveform patterns comprises a sequence of vowel waveform patterns.

12. The method of claim 1, wherein generating the plurality of continuously time-varying acoustic parameters includes:
computing the time-varying intensity value in proportion with the time varying signal value of the continuous time-domain signal; and
generating a time-varying control parameter corresponding to the computed time-varying intensity value.

13. The method of claim 1, wherein generating the plurality of continuously time-varying acoustic parameters includes:
selecting a base frequency;
and generating the time-varying pitch-control parameter in proportion with the selected base frequency and the time varying signal value of the continuous time-domain signal.

14. The method of claim 1, wherein generating the plurality of continuously time-varying acoustic parameters includes:
selecting a sonic identity in proportion with a spatial location in the brain of sensing the continuous time-domain signal; and
generating an identity-control parameter in proportion with the selected sonic identity,
wherein the audio synthesizer is further driven using the identity-control parameter to produce the representation of the acoustic signal corresponding to the brain activity of the subject.

15. The method of claim 1 wherein the continuous audio playback of the representation of the acoustic signal represents a first sound modulation in response to a normal brain state, wherein the continuous audio playback of the representation of the acoustic signal represents a second sound modulation in response to a physiologically harmful brain event, and wherein the first sound modulation and second sound modulation are audibly distinct.

16. A digital processor system for sonifying brain signals, the digital processor system comprising:
at least one processing unit;
an interface for obtaining a continuous time-domain sensor signal representing brain activity of a subject from at least one sensor;
a non-transitory memory storing a plurality of modules which when executed by the at least one processing unit perform processing operations, the plurality of modules comprising:
a plurality of signal modulators directed to generate a plurality of continuously time-varying acoustic parameters from a continuous time-domain signal representing brain activity, the plurality of continuously time-varying acoustic parameters including a vowel-control parameter, an intensity-control parameter, and a pitch-control parameter, wherein at least three of the parameters in the plurality of continuously time-varying acoustic parameters are continuously modulated in proportion with at least the continuous time-varying value of the time-domain signal during concurrent generation;

a voice synthesizer directed to combine the concurrently generated plurality of continuously time-varying acoustic parameters, including the vowel-control parameter, the intensity-control parameter, and the pitch-control parameter, to produce a representation of an acoustic signal corresponding to the brain activity represented by the sensor continuous time-domain signal and for performing continuous audio playback of the representation of the acoustic signal; and at least one speaker to audibly provide the representation of the acoustic signal.

17. The system of claim 16 wherein the continuous audio playback of the representation of the acoustic signal represents a first sound modulation in response to a normal brain state, wherein the continuous audio playback of the representation of the acoustic signal represents a second sound modulation in response to a physiologically harmful brain event, and wherein the first sound modulation and second sound modulation are audibly distinct.

18. A system for sonifying brain signals, comprising:
at least one speaker;
at least one processor;
a non-transitory memory; and
at least one program, wherein the at least one program is stored in the non-transitory memory and configured to be executed by the at least one processors, the at least one program including instructions for:

generating a plurality of continuously time-varying acoustic parameters from a continuous time-domain signal representing brain activity, the plurality of continuously time-varying acoustic parameters including a vowel-control parameter, an intensity-control parameter, and a pitch-control parameter, wherein at least three parameters in the plurality of continuously time-varying acoustic parameters are continuously modulated in proportion with at least the time-varying value of the time-domain signal during concurrent generation;

driving an audio synthesizer using the concurrently generated plurality of continuously time-varying acoustic parameters, including the vowel-control parameter, the intensity-control parameter, and the pitch-control parameter, to produce a representation of an acoustic signal corresponding to the brain activity represented by the continuous time-domain signal;

performing continuous audio playback of the representation of the acoustic signal, wherein performing the continuous audio playback comprises audibly providing, with at least one speaker, the representation of the acoustic signal.

19. The system of claim 18, wherein performing continuous audio playback of the representation of the acoustic signal further comprises vocalization of the representation of the acoustic signal.

20. A method of sonifying brain signals using a digital processor system that comprises at least one processing unit, the method comprising:

generating, using the digital processor system, a plurality of continuously time-varying acoustic parameters from a continuous time-domain signal representing the brain activity of a subject, the plurality of continuously time-varying acoustic parameters including a vowel-control parameter, an intensity-control parameter, and a pitch-control parameter, wherein at least three of the parameters in the plurality of continuously time-varying acoustic parameters are continuously modulated in proportion with at least the continuous time varying signal value of the time-domain signal during concurrent generation;

driving, with the digital processor system, a vocal synthesizer using the concurrently generated plurality of continuously time-varying acoustic parameters to produce a vocalized representation of an acoustic signal corresponding to the brain activity of the subject represented by the continuous time-domain signal; and performing continuous audio playback of the vocalized representation of the acoustic signal using the digital processor system, wherein performing the continuous audio playback comprises audibly providing, with at least one speaker, the vocalized representation of the acoustic signal, wherein the vocalized representation of the acoustic signal manifests at least one audibly discernible variation across a plurality of stages of a brain activity event according to the continuously time-varying plurality of acoustic parameters.

21. The method of claim 20 wherein the continuous audio playback of the representation of the acoustic signal represents a first sound modulation in response to a normal brain state, wherein the continuous audio playback of the representation of the acoustic signal represents a second sound modulation in response to a physiologically harmful brain event, and wherein the first sound modulation and second sound modulation are audibly distinct.

* * * * *